United States Patent [19]
DeRudder

[11] Patent Number: 5,137,688
[45] Date of Patent: Aug. 11, 1992

[54] IRRADIATED ARTICLES MOLDED FROM POLYCARBONATE-POLYAMIDE BLENDS

[75] Inventor: James L. DeRudder, Mt. Vernon, Ind.

[73] Assignee: General Electric Company, Mt. Vernon, Ind.

[21] Appl. No.: 619,564

[22] Filed: Nov. 29, 1990

[51] Int. Cl.⁵ .................. A61L 2/08; C08L 69/00; C08L 77/00
[52] U.S. Cl. ............................ 422/22; 525/432; 525/433
[58] Field of Search .................... 525/432, 433; 422/22

[56] References Cited

U.S. PATENT DOCUMENTS

| | | | |
|---|---|---|---|
| 4,749,754 | 6/1988 | Gallucci | 525/433 |
| 4,778,656 | 10/1988 | Allen | 525/439 |
| 4,798,874 | 1/1989 | Maresca | 525/433 |
| 4,880,854 | 11/1989 | Auakian | 523/136 |

FOREIGN PATENT DOCUMENTS

| | | |
|---|---|---|
| 135659 | 4/1985 | European Pat. Off. . |
| 204754 | 9/1987 | Japan ..................... 422/22 |

Primary Examiner—James J. Seidleck
Assistant Examiner—David Buttner
Attorney, Agent, or Firm—Joseph T. Eisele; Martin B. Barancik

[57] ABSTRACT

Thermoplastic articles molded from amorphous polyamide and polycarbonate resin blends exhibit improved color when irradiated with ionizing radiation.

12 Claims, No Drawings

IRRADIATED ARTICLES MOLDED FROM POLYCARBONATE-POLYAMIDE BLENDS

BACKGROUND OF THE INVENTION

The invention relates to irradiated articles molded from thermoplastic molding compositions and more particularly relates to articles molded from compositions of blended aromatic polycarbonate resins and polyamide resins, sterilized by ionizing radiation.

Synthetic polymeric resins have been used increasingly to mold articles useful in medicine and surgery. Examples of such articles include containers, packaging, instruments, prosthetics, tubing, and working components of treatment apparatus. the selection of a particular polymeric resin will depend on the physical properties required in the molded article.

One property necessary to many medical and surgical articles molded from thermoplastic polymeric resins, is their receptivity to sterilization procedures. A commonly preferred sterilization technique is exposure to ionizing radiation. Unfortunately, ionizing radiation may adversely impact some polyaeric resins in ways unacceptable to some uses.

For example, polycarbonate resins have many properties which are advantageous to their use in many medical and surgical devices or articles. However, upon exposure to ionizing radiation they change from a normally desired transparency and clarity to a yellowed coloration. In addition, this yellow color formed is unstable and continuously changes with increasing time after gamma ray exposure. Aesthetically, the yellowed coloration and the continuously changing color are not always acceptable.

A number of compounds have been prepared as additives to polycarbonate resins, to inhibit the yellowing of articles molded from polycarbonates and subjected to ionizing radiation. Representative of these additives are those described in the U.S. Pat. Nos. 4,624,972 (Nace); 4,657,949 (Nace); 4,757,104 (Nace); and 4,804,692 (Lundy et al.). However, the presence of any additive on a polycarbonate resin molding composition generally has an effect on other desirable physical properties.

Another strategy for reducing the yellowing of a polycarbonate resin upon exposure to ionizing radiation is described in the U.S. Pat. No. 4,778,656 (Allen et al, 1988). The method entails blending the polymer with another polymer, which has the effect of improving ionizing radiation resistance of the polycarbonate. Examples of the additive polymers are polyester, polysulfone-carbonates and certain copolyesters. Like the previously described yellowing inhibitors, these additive polymers also affect physical properties in articles molded from blends of the mixed polymers. This is not to say that some combinations of polymeric resins are not applicable for molding articles useful in medical and surgical procedures. In fact, blends of polycarbonates and polyamides have gained some interest in other areas because of their unique properties.

Blends of polycarbonate resin and polyamide resin, such as amorphous polyamide, have been found to possess a unique combination of properties which include, for example, high resistance to permeation by gases such as oxygen and carbon dioxide, low water absorption, high creep resistance, and good organic solvent resistance; see for example U.S. Pat. No. 4,749,754 (Gallucci et al, 1988).

SUMMARY OF THE INVENTION

The invention comprises an article molded from a thermoplastic molding composition, which comprises;
from about 10–90 percent by weight of an aromatic polycarbonate resin; and
from about 10–90 percent by weight of an amorphous polyamide resin;
said article having been subjected to sterilization by ionizing ray.

The term "sterile" and "sterilizing" as used throughout the specification and claims is not according to the classical definition formulated by the Council on Pharmacy and Chemistry of the American Medical Association, but rather means the absence (or killing) of undesirable microorganisms within the limits prescribed by the United States Pharmacopia XXII (1990). The methods of determining sterility and the specification for sterility may be in accordance with the U.S. Pharmacopia XXII; see (71) pages 1483–1488.

The term "ionizing-ray" as used throughout the specification and claims means ionizing radiation. The term "ionizing radiation" means radiation possessing an energy at least sufficient to produce ions or to break chemical bonds and thus includes radiations such as "ionizing particle radiation" as well as radiations of the type termed "ionizing electromagnetic radiation".

The term "ionizing particle radiation" is used to designate the emission of electrons or highly accelerated, relatively heavy, nuclear particles such as protons, neutrons, alpha particles, deuterons, beta particles, or their analogs directed in such a way that the particle is projected into the mass to be irradiated. Charged particles can be accelerated by the aid of voltage radiants by such devices as accelerators with resonance chambers, Van der Graaff generators, insulating core transformers, betatrons, synchrotrons, cyclotrons and the like. Neutron radiation can be produced by bombarding a selected light metal such as beryllium with positive particles of high energy. Particle radiations can also be obtained by the use of an atomic pile, radioactive isotopes or other natural or synthetic radioactive materials.

"Ionizing electromagnetic radiation" is produced when a metallic target such as tungsten is bombarded with electrons of suitable energy. This energy is conferred to the electrons by potential accelerators over 10,000 electron volts. In addition to radiations of this type, commonly called x-ray, an ionizing electromagnetic radiation suitable for the practice of this invention may be obtained by means of a nuclear reactor (pile) or by the use of natural or synthetic radioactive material, for example, cobalt 60. The use of cobalt 60 as a source of ionizing radiation, producing gamma rays, is preferred in the method of the present invention.

The articles of the invention are useful for a wide variety of purposes such as, for example, medical instruments and devices.

DETAILED DESCRIPTION OF THE PREFERRED EMBODIMENTS OF THE INVENTION

The aromatic polycarbonate resins suitable for use herein may be prepared by reacting a dihydric phenol with a carbonate precursor, such as phosgene, a haloformate or a carbonate ester. Generally speaking, such carbonate polymers may be typified as possessing recurring structural units of the formula:

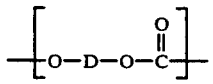

wherein D is a divalent aromatic radical of the dihydric phenol employed in the polymerization reaction. Preferably, the carbonate polymers used to provide the resinous compositions of the invention have an intrinsic viscosity (as measured in methylene chloride at 25° C.) ranging from about 0.30 to about 1.40 dl/g. The dihydric phenols which may be employed to provide such aromatic carbonate polymers are mononuclear or polynuclear aromatic compounds, containing as functional groups two hydroxy radicals, each of which is attached directly to a carbon atom of an aromatic nucleus. The preferred polycarbonate resin for use herein is a homopolymer derived from 2,2-bis- (4-hydroxyphenyl) propane and a carbonate precursor.

These aromatic polycarbonates may be manufactured by known processes, such as by the methods set forth in U.S. Pat. Nos. 4,018,750 and 4,123,436 where a dihydric phenol is reacted with a carbonate precursor; or by transesterification processes such as are disclosed in U.S. Pat. No. 3,154,008, as well as other processes known to those skilled in the art.

Included within the term "polycarbonates", for the purposes of this invention are the poly (ester-carbonate) resins. These resins may generally be described as polymers comprising recurring carbonate groups,

and aromatic carbocyclic groups in the linear polymer chain, in which at least some of the carboxylate groups and at least some of the carbonate groups are bonded directly to ring carbon atoms of the aromatic carbocyclic groups. These poly (ester-carbonate) polymers, in general, are prepared by reacting an aromatic difunctional carboxylic acid or ester forming derivative, a dihydric phenol and a carbonate precursor.

The preparation of poly (ester-carbonates) which may be employed in the compositions of the present invention is described in U.S. Pat. Nos. 3,030,331; 3,169,121; 3,207,814; 4,194,038 and 4,156,069 incorporated herein by reference.

The poly (ester-carbonates) which are preferred in the practice of the present invention include the aromatic poly (ester-carbonates) derived from dihydric phenols, aromatic dicarboxylic acids or their reactive ester forming derivatives such as the aromatic diacid halides, and phosgene. A particularly useful class of aromatic poly (ester-carbonates) is that derived from bisphenol-A, isophthalic acid, terephthalic acid, or a mixture of isophthalic acid and terephthalic acid, or the reactive derivatives of these acids such as terephthaloyl dichloride, isophthaloyl dichloride, or a mixture of isophthaloyl dichloride and terephthaloyl dichloride, and phosgene. The molar proportion of ester units in the poly (ester-carbonate) is generally from about 25 to 90 mole percent and preferably about 35 to 80 mole percent. The molar range of terephthalate units, with the remainder of the copolymer ester units preferably comprising isophthalate units, is generally from about 2 to about 90 percent, and preferably from about 5 to about 50 percent.

Typical dihydric phenols useful in formulating the polycarbonate resins, as described above, may be represented by the general formula:

in which A is an aromatic group such as phenylene, biphenylene, naphthylene or anthrylene. E may be an alkylene or alkylidene group such as isopropylidene, butylene, butylidene, isobutylidene, amylene, isoamylene, amylidene, isoamylidene, and generally has from one to twelve carbon atoms, inclusive. Where E is an alkylene or alkylidene group, it may also consist of two or more alkylene or alkylidene groups, connected by a non-alkylene or non-alkylidene group such as an aromatic linkage, a tertiary amino linkage, an ether linkage, a carbonyl linkage, or by a sulfur-containing linkage such as sulfide, sulfoxide and sulfone. In addition, E may be a cycloaliphatic group of five to twelve carbon atoms, inclusive (e.g. cyclopentyl, cyclohexyl), or a cycloalkylidene of five to twelve carbon atoms, inclusive, such as cyclohexylidene; a sulfur-containing linkage, such as sulfide, sulfoxide or sulfone; an ether linkage; a carbonyl group; a direct bond; or a tertiary nitrogen group. Other groups which E may represent will occur to those skilled in the art. R is hydrogen or a monovalent hydrocarbon group such as alkyl of one to eight carbon atoms, inclusive (methyl, ethyl, propyl); aryl (phenyl, naphthyl); aralkyl (benzyl, ethylphenyl); or cycloaliphatic of five to twelve carbon atoms, inclusive (cyclopentyl, cyclohexyl). Y may be an inorganic atom such as chlorine, bromine, fluorine; an organic group such as the nitro group; an organic group such as R above; or an oxy group such as OR, it being only necessary that Y be inert to and unaffected by the reactants and the reaction conditions. The letter m is any whole number from and including zero through the number of positions on A available for substitution; p is any whole number from and including zero through the number of available positions on E; t is a whole number equal to at least one; and s is any whole number from and including zero to twenty.

In the typical dihydric phenol compound represented by Formula above, when more than one Y substituent is present, they may be the same or different. The same is true for the R substituent. Where s is greater than one, E can be the same or different. Where E is a direct bond, the aromatic rings are directly joined with no intervening alkylene or other bridge. The positions of the hydroxyl groups and Y on the aromatic nuclear residues, A, can be varied in the ortho, meta, or para positions; and the groupings can be in a vicinal, nonsymmetrical or symmetrical relationship, where two or more ring carbon atoms of the aromatic hydrocarbon residue are substituted with Y and a hydroxyl group.

Examples of dihydric phenol compounds that may be employed in the above polymers include:
2,2-bis-(4-hydroxyphenyl)propane (bisphenol-A);
2,4'-dihydroxydiphenylmethane;
bis-(2-hydroxyphenyl)methane;
bis-(4-hydroxyphenyl)methane;
bis-(4-hydroxy-5-nitrophenyl) methane;
bis-(4-hydroxy-2,6-dimethyl-3-methoxyphenyl)methane;

1,1-bis-(4-hydroxyphenyl)ethane;
1,2-bis-(4-hydroxyphenyl)ethane;
1,1-bis-(4-hydroxy-2-chl-orophenyl)ethane;
1,1-bis-(2,5-dimethyl-4-hydroxyphenyl)ethane;
1,3-bis-(3-methyl-4-hydroxyphenyl)propane;
2,2-bis-(3-phenyl-4-hydroxyphenyl)propane;
2,2-bis-(3-isopropyl-4-hydroxyphenyl)propane;
2,2-bis-(4-hydroxyphenyl)propane;
2,2-bis-(4-hydroxyphenyl)pentane;
3,3-bis-(4-hydroxyphenyl)pentane;
2,2-bis-(4-hydroxyphenyl)heptane;
bis-(4-hydroxyphenyl)phenylmethane;
bis-(4-hydroxyphenyl)cyclohexymethane;
1,2-bis-(4-hydroxyphenyl)-1,2-bis-(phenyl)propane;
2,2-bis-(4-hydroxyphenyl)-1-phenylpropane; and the like.

Also included are dihydroxybenzenes typified by hydroquinone and resorcinol; dihydroxydiphenyls such as 4,4'-dihydroxydiphenyl; 2,2'-dihydroxydiphenyl; 2,4'-dihydroxydiphenyl; dihydroxynaphthalenes such as 2,6-dihydroxynaphthalene, etc. Also useful are dihydric phenols wherein E is a sulfur-containing radical such as the dihydroxy aryl sulfones exemplified by: bis-(4-hydroxyphenyl)sulfone; 2,4'-dihydroxydiphenyl sulfone; bis-(3,5-dimethyl-4- hydroxyphenyl)sulfone; 5'-chloro-2,4'-dihydroxydiphenyl sulfone; 3-chloro-bis-(4-hydroxyphenyl)sulfone; and 4,4'-dihydroxytriphenyldisulfone; etc. The preparation of these and other useful sulfones are described in U.S. Pat. 2,288,282. Hydroxy terminated polysulfones as well as substituted sulfones using halogen, nitrogen, alkyl radicals are also useful.

Dihydroxy aromatic ethers such as those described in U.S. Pat. No. 3,148,172 are useful as the dihydric phenol herein. The dihydroxy aromatic ethers may be prepared as described in U.S. Pat. No. 2,739,171. Illustrative of such compounds are the following:
4,4'-dihydroxydiphenyl ether;
4,4'-dihydroxytriphenyl ether; the 4,3'-, 4,2'-, 4,1'-, 2,2'-, 2,3'-dihydroxydiphenyl ethers;
4,4'-dihydroxy-2,6-dimethyldiphenyl ether;
4,4'-dihydroxy-2,5-dimethyldiphenyl ether;
4,4'-dihydroxy-3,3'-diisobutyldiphenyl ether;
4,4'-dihydroxy-3,3'-diisopropyldiphenyl ether;
4,4'-dihydroxy-3,3'-dinitrodiphenyl ether;
4,4'-dihydroxy-3,3'-dichlorodiphenyl ether;
4,4'-dihydroxy-3,3'-difluorodiphenyl ether;
4,4'-dihydroxy-2,3'-dibromodiphenyl ether;
6,6'-dihydroxydinaphthyl-2,2'-ether;
6,6'-dihydroxy-5,5'-dichlorodinaphthyl-2,2'-ether;
4,4'-dihydroxypentaphenyl ether;
4,4'-dihydroxy-2,6-dimethoxydiphenyl ether; and
4,4-dihydroxy-2,5-diethoxydiphenyl ether.

Mixtures of the dihydric phenols can also be employed, and where dihydric phenol is mentioned herein, mixtures of such materials are considered to be included. Other dihydric phenols which are suitable are disclosed in U.S. Pat. Nos. 2,999,835; 3,028,365; 3,334,154; 4,131,575.

The carbonate precursor used to produce the polycarbonate resins may be either a carbonyl halide, a carbonate ester, or a haloformate. The carbonyl halides which can be employed are carbonyl bromides. Typical of the carbonate esters are diphenyl carbonate, di(halophenyl)carbonates such as di(chlorophenyl)carbonate, di(bromophenyl)carbonate, di(trichlorophenyl)carbonate, di(tribromophenyl)carbonate, di(alkylphenyl)carbonate such as di(tolyl) carbonate, phenyltolyl carbonate, chloronaphthyl chlorophenyl carbonate, and the like. The haloformates suitable for use herein include bishaloformates of dihydric phenols such as bischloroformates of hydroquinone or glycols such as bis-haloformates of ethylene glycol, neopentyl glycol, and polyethylene glycol. While other carbonate precursors will occur to those skilled in the art, carbonyl chloride, also know as phosgene, is preferred.

The aromatic difunctional carboxylic acids suitable for producing poly (ester-carbonates) may be represented by the general formula:

$$HOOC-Z-COOH \qquad (II)$$

wherein Z represents an aromatic radical such as phenylene, naphthylene, biphenylene, substituted phenylene; two or more aromatic groups connected through non-aromatic linkages such as those defined by E in Formula I; or a divalent aliphatic-aromatic hydrocarbon radical such as an aralkyl or alkaryl radical. For purposes of the present invention, the aromatic dicarboxylic acids or their reactive derivatives such as, for example, the acid halides or diphenyl esters, are preferred. Thus, in the preferred aromatic difunctional carboxylic acids, as represented by Formula II, Z is an aromatic radical such as phenylene, biphenylene, naphthylene, substituted phenylene, etc. Some non-limiting examples of suitable aromatic dicarboxylic acids which may be used in preparing the poly (ester-carbonate) of the instant invention include phthalic acid, isophthalic acid, terephthalic acid, homophthalic acid, o-, m-, and p-phenylenediacetic acid, and the polynuclear aromatic acids such as diphenyl dicarboxylic acids and isomeric naphthalene dicarboxylic acids. The aromatics may be substituted with Y groups in the same manner as the Formula I aromatics are substituted. Of course, these acids may be used individually or as mixtures of two or more different acids.

The polyamides employed in this invention are the amorphous polyamides. Included within the term "amorphous polyamides" as used herein and in the claims are those polyamide polymers having a heat of fusion of about 1 calorie per gram or less, as determined by differential scanning calorimetry (DSC). Such amorphous polyamide polymers may have a degree of crystallinity as high as 5% and for some polyamides, the degree of crystallinity may be even higher. Preferably, the amorphous polyamides will not have a crystallization transition or crystalline melting transition temperature and therefor, no measurable degree of crystallinity.

High levels of crystallinity within a sample are obtained from molecular symmetry, hydrogen bonding and linearity within the polymers. Where the polyamide polymers exhibit these characteristics, it is difficult to obtain samples in the amorphous state. Portions of a polymer may exhibit these characteristics and provide "islands" of crystallinity. To obtain amorphous polyamides, it is within the skill of a person knowledgeable in the art to avoid symmetry and linearity when producing polymers. Symmetry in the polymer may be avoided by utilizing a variety of monomers in the reaction mixture. Branched-chain monomer segments may be used instead of those having linear segments and hydrogen bonding can be avoided to some degree by utilizing aromatic groups. It should be noted that chain stiffness will also contribute to crystallinity, rendering hydrogen bonding unnecessary for crystallinity where chain stiffness and symmetry are sufficiently high. Ring containing polyamides, especially aromatic ring containing polyamides such as polyterephthalamides, have high stiffness and symmetry and tend to crystallinity. Side chain substitutions on the polymer backbone, such as the use of a methyl group to disrupt regularity and hydrogen bonding, may be employed. Odd chain diamines, diacids and meta aromatic substitution, may prevent crystallization. Symmetry may also be disrupted through copolymerization by using more than one diamine, diacid or monoamino-monocarboxylic acid. In the case of copolymers, those monomers which normally are polymerized to produce crystalline homopolymers such as nylon 6; 6/6; 11; 12; 6/3;6/4;6/10 or 6/12, may be copolymerized to produce a random amorphous copolymer.

Examples of amorphous polyamides contemplated to be used in this invention include, but are not limited to, those having repeating units of a formula selected from the group consisting of

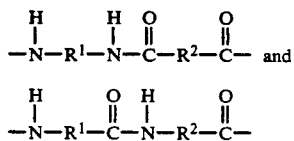

wherein $R^1$ and $R^2$ are different divalent organic radicals selected from the group consisting of $C_2$–$C_{15}$ alkylene radicals, $C_3$–$C_{18}$ cyclo alkylene radicals and $C_6$–$C_{20}$ arylene radicals. Mixed alkylene-cycloalkylene radicals or alkylene-arylene or arylene-alkylene radicals of $C_4$–$C_{30}$ are also considered to be within the scope of the terms "cycloalkylene" and "arylene", respectively.

These amorphous polyamides may be prepared by polymerization of diamines having the formula:

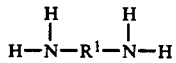

with dicarbonyl compounds such as dicarboxylic acids, esters or chlorides of the formula:

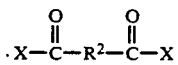

wherein X is chlorine, hydroxy, $C^1$–$C_3$ alkoxy or $C_6$–$C_{20}$ aryloxy and $R^1$ and $R^2$ are as defined above. Typically, equimolar portions of the diamine and dicarboxylic acid are utilized. Slight departures from the equimolar proportions can be tolerated. Examples of suitable diamines include trimethylene diamine, tetramethylene diamine, pentamethylene diamine, hexamethylene diamine, isomeric trimethylhexamethylene diamine, 2,2-bis (p-aminocyclohexyl) propane, bis-(4-aminocyclohexyl)methane, bis(4-amino-3-methylcyclohexyl) methane, bis (4-aminophenyl) methane, metaphenylene diamine, paraphenylene diamine, meta-xylylene diamine, para-xylylene diamine and the like.

The dicarboxylic acids/esters include sebacic acid, suberic acid, glutaric acid, pimelic acid, adipic acid, octadecanedioic acid, terephthalic acid, isophthalic acid, and azelaic acid.

Preferred combinations of acid and amine include terephthalic acid with trimethyl-hexamethylene diamine; adipic acid plus azelaic acid with 2,2-bis-(p-amino-cyclohexyl) propane; terephthalic acid with bis(4-aminocyclohexyl) methane; isophthalic acid with hexamethylene diamine and terephthalic acid and isophthalic acid with hexamethylene diamine and combinations thereof.

An alternative method for preparing the amorphous polyamides utilized in this invention is to polymerize two different monoamino-monocarbonyl compounds of each formula:

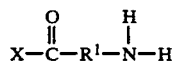

and

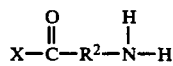

wherein X, $R^1$ and $R^2$ are defined above. Lactam structures for these monoamino-monocarboxylic acids may also be utilized either alone or with the monoamino-monocarboxylic acids. The lactam structures are a ring structure formed by self-reaction of the amine and acid groups. Examples of these monoamino- monocarboxylic acids and their lactams include: aminocaproic acid, butyrolactam, pivalolactam, carpolactam, capryilactam, enantholactam, undecanolactam, dodecanolactam, 3-aminobenzilic acid and 4-aminobenzilic acid. Mixtures of the lactams with diamines and dicarboxylic acids (and their derivatives) will also produce amorphous polyamides. Mixtures, random copolymers or block copolymers of two or more to the amorphous polyamides are within the scope of this invention also.

Particular examples of amorphous polyamides for use in the invention include, but are not limited to:

PACP-9/6, which is a 50:50 mole ratio copolymer of 2,2'bis (4-aminocyclohexyl) propane and a 60/40 weight percent mixture of azelaic acid and adipic acid. A more detailed description of the preparation of this polymer is found in U.S. Pat. No. 3,840,501, which is incorporated herein by reference;

Zytel ® 330 and Selar ® PA, which are amorphous polyamides derived from hexamethylene diamine and mixtures of terephthalic acid and isophthalic acid. These amorphous polyamides are available from E. I. DuPont.

It is also to be understood that these amorphous polyamides include the toughened or the super-tough polyamides. These polymers are available commercially from E. I. duPont under the tradename Zytel ST or may be prepared in accordance with U.S. Pat. Nos. 4,174,358, 4,474,927, or 4,346,194, incorporated herein by reference. The super-tough polyamides are prepared by blending the polyamide polymers with one or more polymeric elastomeric toughening agents. Suitable toughening agents are disclosed in the above patents as well as in Caywood Jr., U.S. Pat Nos. 3,884,882 and Swiger U.S. 4,147,740, incorporated herein by reference. Typically, these elastomeric polymers and copolymers are straight chained or branched as well as graft copolymers and also include core-shell graft copolymers. They are characterized as having incorporated therein a monomer having functional and/or active polar groupings capable of interacting or adhering to the polyamide matrix so as to enhance the toughness of the polyamide polymer.

The above polyamides may be prepared by any of several well known processes. Salt polymerization reacts an amine group and a carboxylic acid group to form an amide group with the concomitant elimination of water. Oligomeric salts are formed, water is removed, and polymerization proceeds at higher temperatures. Other processes include solution or interfacial polymerization. These processes recommend reacting an amine with an acid chloride to form a polyamide with the loss of hydrochloric acid. A preferred process is melt polymerization, by amine-ester interchange. A solvent may be added, or the process may be performed without a solvent as described in U.S. Pat., No. 4,567,249, hereby incorporated by reference.

Polyamides for use herein may have a number average molecular weight ranging from about 12,000 to about 60,000 g/mole, preferably from about 15,000 to about 40,000 g/mole, and most preferably from about 20,000 to about 35,000 g/mole, as determined by membrane osmometry; J. Herold, G. Meyerhoff, Evr. Polym, J. 15,525 (1979). Alternately, preferred polyamides may be described as having an intrinsic viscosity ranging from about 0.5 to about 1.6 dl/g, preferably from about 0.7 to about 1.4 dl/g, and most preferably from about 0.9 to about 1.2 dl/g as measured with 40 mg per 10 cc of a 60/40 weight ratio phenol/tetrachloroethylene solvent at 30° C.

Blends of polycarbonate and polyamide resins are generally obtainable in all proportions relative to each other. Consequently, articles molded from blends having a weight ratio of polyamide to polycarbonate in the range of 1:9 to 9:1 are within the scope of this invention. By controlling the proportions of the polyamide and polycarbonate relative to each other, articles having certain properties may be readily obtained. The weight ratio of polycarbonate to polyamide is preferably about 1:1.

The molding compositions of the invention may contain other components such as stabilizers, flame retardants, mold release agents, foaming agents, pigments, and other thermoplastic resins such as polyesters, polyphenylene ethers, polyimides and the like.

The compositions of the invention may also contain fillers and reinforcing fibers such as, for example, glass and carbon. The fillers may include, for example, silica, talc, clay, mica, calcium sulfate and calcium carbonate. The amount of such additives present is dependent upon the desired effect and it is within the knowledge of those skilled in the art to determine the appropriate amounts.

Advantageously, the molding compositions used herein also include an impact-modifying proportion of an impact-modifier.

The impact modifiers employed in this invention may be polyamide-polyether block copolymers which may be represented by the schematic formula:

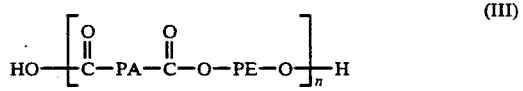

(III)

wherein PA represents the polyamide segment, PE represents a polyether segment and n is an integer such that the block copolymer has a weight average molecular weight ($M_w$) of from about 5,000 to about 100,000. Polyamide-polyether block copolymers of the class described above are generally well known and may be prepared for example by the condensation reaction of a prepolyamide and a polyoxyalkylene glycol, by conventional technique; see for example the preparative methods described in U.S. Pat. Nos. 4,208,493; 4,230,838; 4,361,680; and 4,331,786, all of which are incorporated herein by reference thereto. The polyamide-polyether block copolymers so prepared are commercially available and may be wide ranging in their make-up from a wide range of prepolyamides and polyoxyalkylene glycols.

The prepolyamide may have an inherent viscosity of at least about 0.1 (determined at a temperature of 25° C. using 0.25 gm of polymer per 100 ml. of a solvent consisting of 60 percent phenol and 40 percent by volume of tetrachloroethane) and will be terminated with acid or amine groups. The prepolyamide may be the polymerization product of a difunctional diamine component and a difunctional dicarboxylic acid.

In general, any aliphatic, alicyclic, or aromatic polyfunctional amine or mixture of amines can be used to prepare the prepolyamide. Examples of such polyamines are diamines which include polymethylenediamines of the formula $H_2N(CH_2)_xNH_2$, wherein x is a positive integer of from 2 to 12 (such as dimethylenediamine, trimethylenediamine, tetramethylenediamine, pentamethylenediamine, hexamethylenediamine, heptamethylenediamine, octamethylenediamine, nonamethylenediamine, decamethylenediamine, undecamethylenediamine, and dodecamethylenediamine); 1,1-, 1,2-, 1,3-, and 1,4-cyclohexane-bis- (methylamines); o-, m-, and p-xylenediamines; 1,2-, 1,3- and 1,4-cyclohexanediamines; 3-methylhexa-methylenediamine; 3-methylheptamethyenediamine; 2,4-dimethylhexamethylenediamine; 2,4-toluenediamine; p,p'-diphenyldiamine; 1,4-dimethyl-3,5-diaminobenezene; 2,5-norcamphane bis-(methylamine); o-, m-, and p-phenylenediamines; 2,5-,2,6-, and 2,7-naphthalenediamines; benzidine; 4,4'-methylenedianiline; and 3,4'-diaminodiphenyl. The N,N'-diphenyldiamines of U.S. Pat. No. 3,297,656 can also be employed.

In general, any aliphatic, alicyclic, and aromatic difunctional dicarboxylic acid can be used to prepare the prepolyamide. Examples of such acids include oxalic; malonic; dimethylmalonic; succinic; glutaric; adipic; trimethyladipic; pimelic;2,2-dimethylglutaric; azelaic; sebacic; suberic; fumaric; maleic; itaconic; 1,3-cyclopentanedicarboxylic; 1,2-cyclohexanedicarboxylic; 1,3-cyclohexanedicarboxylic; 1,4-cyclohexanedicarboxylic; phthalic; terephthalic; isophthalic; t-butyl isophthalic; 2,5-norbornanedicarboxylic; 1,4-naphthalenedicarboxylic; diphenic; 4,4'-oxydibenzoic; diglycolic; thiodipropionic; 2,2,4-trimethyladipic; 4,4'-sulfonyldibenzoic; 2,5-naphthalenedicarboxylic; 2,6-naphthalenedicarboxylic; and 2,7-naphthalenedicarboxylic acids.

The prepolyamides are prepared by conventional and known techniques for the preparation of a polyamide resin and may have a weight average molecular weight of from 300 to 15,000.

The polyoxyalkylene glycols used to prepare the polyamidepolyether block copolymers used as impact-modifiers in the present invention are well known compounds and include for example polyoxypropylene glycol, polyoxyethylene glycol and polyoxybutylene glycol, each of which are commercially available and have weight average molecular weights ($M_w$) of from 200 to 15,000. The preferred polyoxyalkylene glycols may also be characterized by an inherent viscosity of from 0.1 to 0.5 (determined as described above for the determination of inherent viscosity of the prepolyamide). The polyether can have diol and/or diamine end groups, amino end groups can be prepared through cyanoethylation of the polyether followed by hydrogenation. Other modifications of the polyether end groups can also be made to facilitate bonding to the polyamide blocks.

A preferred impact-modifying polyamide-polyether block copolymer employed in the compositions and the method of the invention are of the formula (III) given above, wherein PA represents a saturated amide sequence formed from a lactam or an amino acid having a hydrocarbon chain containing from 4 to 14 carbon atoms, inclusive, or from a diamine and a dicarboxylic acid each having from 4 to 40 carbon atoms, inclusive; said amide having a weight average molecular weight of from 300 to 15,000; and PE represents a polyether sequence formed from a polyoxyalkylene glycol having a weight of from 200 to 15,000. Most preferred, the copolymer will be one wherein the proportion by weight of polyoxyalkylene glycol with respect to the total weight of the copolymer is form 5 to 85 percent. In general, these preferred block copolymers will have an intrinsic viscosity of from 0.8 to 2.05 as measured in meta-cresol at 25° C. (initial concentration: 0.8 gms/100 ml).

The above described impact-modifying copolymer can be present in a wide range of concentrations. However, to obtain the most useful blends, it is preferable to maintain the concentration of impact-modifying copolymer to less than 40% by weight of the total composition of the invention. Concentrations of from to 30 weight percent to impact-modifying copolymer provide a significant enhancement in impact strength without a significant loss to other desirable physical properties of the blend, such as heat distortion temperature. Concentrations below 5% by weight can be expected to have an enhancing effect on impact strength but at levels which correspond to the low concentration. The most preferred concentrations fall within the highest impact modifying effect varying with the ratio of polycarbonate to polyamide, as discussed above.

Another class of polycarbonate impact modifier is represented by selectively hydrogenated linear, sequential or radial teleblock copolymers of a vinyl aromatic compound (A) and (A')n and an olefinic elastomer (B) of the A—B—A'; A (B—A—B )$_n$A; A (B—A )$_n$B; or B [( A—B$_n$) B]$_4$ type wherein n is an integer of from 1 to 10 inclusive.

The selectively hydrogenated linear block copolymers are well known as are methods of their preparation, and they are commercially available. The selectively hydrogenated linear block copolymers are well known and are described by Haefele et al, U.S. Pat. No. 3,333,024, which is incorporated herein by reference.

Prior to hydrogenation, the end blocks of these copolymers comprise homopolymers or copolymers preferably prepared from alkenyl aromatic hydrocarbons and particularly vinyl aromatic hydrocarbons wherein the aromatic moiety may be either monocyclic or polycyclic. Typical monomers include styrene, alpha methyl styrene, vinyl xylene, ethyl vinyl xylene, vinyl naphthalene, and the like, or mixtures thereof. The end block (A) and (A$^1$), may be the same or different. They are preferably selected from styrene, α-methyl styrene, vinyl toluene, vinyl xylene, vinyl naphthalene, especially styrene. The center block (B) may be derived from, for example, butadiene, isoprene, 1,3-pentadiene, 2,3,dimethyl butadiene, and the like, and it may have a linear, sequential or teleradial structure.

The ratio of the copolymers and the average molecular weights can vary broadly although the molecular weight center block should be greater than that of the combined terminal blocks. It is preferred to form terminal blocks A having weight average molecular weights of 2,000 to 100,000 and center block B, e.g., a hydrogenated polybutadiene block with a weight average molecular weight of 25,000 to 1,000,000. Still more preferably, the terminal blocks may have weight average molecular weights of 8,000 to 60,000 while the hydrogenated polybutadiene polymer blocks have a weight average molecular weight between 50,000 and 300,000. The terminal blocks will preferably comprise 2 to 60% by weight, or more, preferably, 15 to 40% by weight, of the total block co-polymer. The preferred copolymers will be those formed from a copolymer having a hydrogenated/ saturated polybutadiene center block wherein 5 to 55%, or more, preferably, 30 to 50% of the butadiene carbon atoms, are vinyl side chains.

The hydrogenated copolymers will have the average unsaturation reduced to less than 20% of the original value. It is preferred to have the unsaturation of the center block B reduced to 10%, or less, preferably 5% of its original value.

The block copolymers are formed by techniques well known to those skilled in the art. Hydrogenation may be conducted utilizing a variety of hydrogenation catalysts such as nickel on kieselguhr, Raney nickel, copper chromate, molybdenum sulfide and finely divided platinum or other noble metals on a low surface area carrier.

Hydrogenation may be conducted at any desired temperature or pressure, from atmospheric to 3000 psig, the usual range being between 100 and 1,000 psig at temperatures from 75 F. to 600 F. for times between 0.1 and 24 hours, preferably from 0.2 to 8 hours.

Hydrogenated block copolymers such as Kraton ® G-6500, Kraton ® G-6521, Kraton ® G-1650 and Kraton ®G-1652 are available from Shell Chemical Company, Polymers Division. Kraton ® G-1650 and Kraton ® G-1651 are preferred for use in the compositions of the invention. Also usable are the so-called hydrogenated Solprenes of Phillips Petroleum Co., especially the product designated Solprene ®-512.

The radial teleblock copolymers, of which the Solprenes are typical examples, can be characterized as having at least three polymer branches with each branch of the radial block polymer comprising terminal non-elastomeric segments, e.g. (A) and (A$^1$) as defined hereinabove. The branches of the radial block polymer contain a terminal non-elastomeric segment attached to an elastomeric polymer segment, e.g. (B) as defined above. These are described by Marrs, U.S. Pat. No. 3,753,936 and by Zelinski, U.S. Pat. No. 3,281,383, both of which are incorporated herein by reference, and they are selectively hydrogenated by procedures as described above. In any event, the term "selective hydrogenation" is used herein to contemplate polymers in which the elastomeric blocks (B) have been hydrogenated, but the non-elastomeric blocks (A) and (A$^1$) have been left unhydrogenated, i.e., aromatic.

The selectively hydrogenated copolymer is used in a proportion of from about 1 to 4 parts by weight (preferably 2 parts by weight for each 100 parts of polycarbonate resin.

Preferred as the impact-modifier used in the compositions of the invention are the so-called "ABS" polymers. ABS polymers are defined, for example, in the Modern Plastics Encyclopedia, 1989 edition, page 92, as the family of thermoplastics made from the three monomers acrylonitrile, butadiene and styrene, and more specifically as a mixture (alloy) of styrene-acrylonitrile copolymer with SAN-grafted polybutadiene rubber.

The preferred ABS polymer of high rubber content for use as an impact-modifier is an ABS having greater than 32% rubber content and made by emulsion polymerization, rather than by bulk or suspension polymerization which are processes frequently used to manufacture commercial ABS; an ABS made by emulsion polymerization is U.S. Pat. 2,820,773 (1958) which is incorporated by reference. ABS resins made by emulsion polymerization and having high rubber content are commercially available, for example the following: Novalar made by Nova Polymers, Inc.: a powdered ABS having about 41% butadiene rubber content, a density of 1.04 and a melt flow index of 4.0; and Blendex 301 made by General Electric Company: a powdered ABS having about 34% polybutadiene rubber content, a specific gravity of 0.99 by ASTM D-792 Method A-1, and a heat deflection temperature of 172° F. at 10 mil deflection and 264 psi (annealed) by ASTM D-648.

Impact—modifying agents for use with the polycarbonate compositions of the invention also include the various polyacrylate resins known in the art. For example, suitable polyacrylates can be made in known ways, but are abundantly commercially available from many sources, e.g., Rohm & Haas Chemical Company, Philadelphia, Penna. under the trade designations Acryloid® KM 330, and 7709 XP; Goodyear Tire & Rubber Company, Akron, Ohio under the trade designation RXL® 6886; from American Cyanamid Company, Stamford, Conn., under the trade designation Cyanacryl® 770; from M&T Chemicals Co., Trenton, N.J., under the trade designation Durostrength® 200; and from Polysar Corporation, Canada, under the trade designation Polysar® §1006. In general any of the polyalkyl acrylates described by Brinkman et al., U.S. Pat. No. 3,591,659 can be used, especially those containing units derived from n-butyl acrylate. Preferably, the polyacrylate will comprise a multiple stage polymer having a rubbery first stage and a thermoplastic hard final stage as described in Farnham et al., U.S. Pat. No. 4,096,202 incorporated herein by reference. It has also been found advantageous to add both polyalky acrylate and an acrylate-based core-shell polymer such as Acryloid® KM-330, above-mentioned.

The polyacrylate resin impact modifiers may be added to the compositions of the invention in conventional amounts of from 0.01% to 50% by weight based on the weight of the overall composition and usually in amounts of from 0.01% to 10% by weight on the same basis.

Other representative impact modifiers are the synthetic polymeric resin elastomers such as silicone rubber, polyether rubber and ethylene-propylene-diene rubber; diene rubbers, i.e., homopolymers of conjugated dienes having, e.g. 4 to 8 carbon atoms, such as butadiene, isoprene, norbornene, piperylene and chloroprene; and copolymers of dienes such as ethylene with each other or with styrene, acrylic acid, methacrylic acid, or derivatives thereof (e.g., acrylonitrile, methacrylonitrile, acrylic acid, methacrylic acid, butyl acrylate and methyl methacrylate), or isobutylene.

An impact-modifying proportion of the latter impact modifiers described above is generally within the range of from about 0.05 to 15 parts by weight of the composition, preferably from 3–10 parts, most preferably 4 to 8 parts.

Other impact-modifying agents useful in the compositions of the invention will be appreciated by those skilled in the art.

It will be appreciated by those skilled in the art that an impact modifying proportion of the impact modifier used in the compositions of the invention will be dependent upon the particular modifier selected. In general however, the proportion will be most preferably one within the range of from about 5 to about 20 parts by weight of the polycarbonate.

Preparation of the resin blends used to mold articles of this invention may be accomplished by any conventional blending technique such as, for example, dry blending, melt blending, solution blending and the like. Melt blending may be accomplished in a conventional extruder, from which the admixture may be molded into a part of specific dimensions or further extruded to a film or sheet product.

The blends may be used to mold articles by any conventional thermoforming technique such as by injection molding.

The initially provided molded articles are generally provided hermetically sealed in a moisture-proof, microorganism-impermeable, ionizing ray-permeable container. Preferably, the articles are sealed in pouches, multiple containers such as overwraps or similar containers made of non-metallic materials which will effectively exclude infiltration of microorganisms, gas, vapor and moisture over a time period of several years. Such packaging materials are commercially available in numerous forms of polymeric films, including laminates of 2 or more films. For example, the pouches may be constructed of polyethylene, polypropylene, polyethyleneterephthalate, polyvinyl chloride and like polymeric films for forming hermetically sealed pouches. It will be appreciated that the containers should be initially provided in clean, particulate free condition and they may be pre-sterilized to some extent employing conventional techniques such as ultra-violet radiation and the like.

After the molded articles are sealed in the above-described containers, they are subjected, according to the method of the invention, to a nondestructive (non-degrading), sterilizing dose of an ionizing ray as defined above.

We have found that a non-degrading, sterilizing dose of ionizing radiation for the articles of the invention is advantageously within the range of from about 0.5 to 10.0 megarads; preferably not more than 4.0. Radiation within this dosage range may be carried out at room temperature or below or at elevated temperatures if so desired. The temperature at which radiation is carried out is not critical to the method of the invention. However, practical temperatures are within the range of from about minus 10° to about 50° C. Lower radiation dosages may not be effective in sterilizing the sealed in articles. Higher doses will generally degrade (destroy) either the package container or the article contained therein or both. This, of course, is undesirable. For this reason, preferably the dosage employed for sterilizing the sealed articles is within the range of from about 1 to about 3 megarads, most preferably circa 2.5 megarads.

Irradiation as described above may also be carried out advantageously in the absence of oxidizing agents, i.e.; in an atmosphere having an oxygen concentration which is reduced to such a degree that the quantity of oxygen molecules present is not sufficient to react during irradiation with the articles and their packaging materials. The reduction of the oxygen presence can be obtained by packaging the articles under and in the presence of an inert gaseous atmosphere such as nitrogen by the use of partial vacuum packing. The irradiation in the presence of nitrogen rather than oxygen atmosphere reduces the secondary or "indirect" destructive effects or radicals generated in the presence of oxygen. There is only a "direct" effect of direct bombardment by the ionizing rays.

As mentioned above, gamma radiation produced by cobalt 60 is a preferred ionizing ray for employment in the method of the invention. Gamma radiation produced by cobalt 60 has a high penetrating ability and obviates the need for concern about the thickness of the article to be penetrated. It is well-known that microorganisms exposed to radiation, including gamma radiation, do not always die immediately. In some bacteria, which have been subjected to a radiation dose which prevents their multiplication, many biological functions continue for extended periods of time. For this reason, sterility testing to be carried out as a control mechanism should be delayed for a period of about four days following radiation.

Apparatus for producing ionizing rays and techniques of their application to a wide variety of materials are so well-known that further description need not be given herein. Those skilled in the art will appreciate the techniques of ionizing ray application.

The following examples describe the manner and process of making and using the invention and set forth the best mode contemplated by the inventors of carrying out the invention but are not to be construed as limiting. Where reported, the test results provided were determined by the following test procedures:

Yellowness Index (YI)

According to ASTM test method D-1925.

Sterility

Representative samples of irradiated materials are tested by standard techniques for total plate count. Those samples that are found to be negative are then serially diluted on slant tubes in accordance with the techniques recommended in United States Pharmacopia, XIX, for sterility.

EXAMPLE 1

Polycarbonate/amorphous nylon blends were prepared from a branched polycarbonate reaction product of phosgene and bisphenol-A (Lexan ® 151, General Electric Co., Mount Vernon, Ind.) and a polyamide resin (Selar ® PA, supra). The blends were compounded on a Werner Pfleiderer ZSK 30 mm twin screw extruder at temperatures of from 260°-280° C. The resulting pellets were dried for at least six hours at 110° C. before injection molding into ASTM test specimens (chips) on a 80 ton, 4 oz. injection molding machine. The chips of different thickness, were then irradiated with various doses of ionizing rays from a cobalt 60 source and then tested for yellowness index at various times. The compositions of the various blends (Samples A-F) are set forth immediately below (Note: Samples A, B, D and E are not blends of the invention, but are for comparative purposes). The test results are set forth in the following Tables 1-6, below.

| COMPOSITIONS OF BLENDS | | | |
|---|---|---|---|
| SAMPLE | LEXAN 151 ® (Parts by wgt.) | SELAR PA ® (Parts by wgt.) | SAMPLE THICKNESS (inches) |
| A (Control) | 100 | | 0.125 |
| B (Control) | | 100 | 0.125 |
| C | 50 | 50 | 0.060 |
| D (Control) | | 100 | 0.060 |
| E (Control) | 100 | | 0.250 |
| F | 90 | 10 | 0.250 |

TABLE 1

| COLOR EFFECTS DUE TO GAMMA IRRADIATION AFTER SHORT TERM DARK AGING | | | |
|---|---|---|---|
| SAMPLE (CONTROLS) | GAMMA IRRADIATION EXPOSURE (MRAD) | COLOR CHANGE DUE TO GAMMA IRRADIATION (DELTA YI) | ELAPSED TIME AFTER GAMMA IRRADIATION IS COMPLETED UNTIL COLOR IS MEASURED (DAYS) |
| A | 2.5 | 13.4 | 0.9 |
| A | 2.5 | 13.0 | 0.9 |
| B | 2.5 | −53.1 | 0.9 |
| B | 2.5 | −51.9 | 0.9 |
| A | 5.0 | 36.3 | 1.0 |
| B | 5.0 | −97.2 | 1.0 |
| A | 7.5 | 44.4 | 4.1 |
| B | 7.5 | −78.1 | 4.1 |

Note:
These samples were all stored in the dark until YI measurements were made.

TABLE 2

| COLOR EFFECTS DUE TO GAMMA IRRADIATION AFTER SHORT TERM DARK AGING | | | |
|---|---|---|---|
| SAMPLE (CONTROLS) | GAMMA IRRADIATION EXPOSURE (MRAD) | COLOR CHANGE DUE TO GAMMA IRRADIATION (DELTA TI) | ELAPSED TIME AFTER GAMMA IRRADIATION IS COMPLETED UNTIL COLOR IS MEASURED (DAYS) |
| C | 2.5 | 3.5 | 0.9 |
| C | 2.5 | 2.6 | 0.9 |
| D (control) | 2.5 | −31.7 | 0.9 |
| D (control) | 2.5 | −29.4 | 0.9 |
| C | 5.0 | 6.8 | 1.0 |
| C | 5.0 | 5.9 | 1.0 |
| D (control) | 5.0 | −59.8 | 1.0 |
| D (control) | 5.0 | −59.7 | 1.0 |
| C | 7.5 | 11.6 | 4.1 |
| C | 7.5 | 14.5 | 4.0 |
| D (control) | 7.5 | −44.7 | 4.1 |
| D (control) | 7.5 | −46.3 | 4.0 |

Note:
These samples were all stored in the dark until YI measurements were made.

TABLE 3

| COLOR EFFECTS DUE TO GAMMA IRRADIATION AFTER SHORT TERM DARK AGING | | | |
|---|---|---|---|
| SAMPLE (CONTROLS) | GAMMA IRRADIATION EXPOSURE (MRAD) | COLOR CHANGE DUE TO GAMMA IRRADIATION (DELTA YI) | ELAPSED TIME AFTER GAMMA IRRADIATION IS COMPLETED UNTIL COLOR IS MEASURED (DAYS) |
| E (control) | 2.5 | 22.5 | 0.9 |
| E (control) | 2.5 | 23.2 | 0.9 |
| F | 2.5 | 30.1 | 0.9 |
| F | 2.5 | 31.1 | 0.9 |
| E (control) | 5.0 | 68.3 | 1.0 |
| E (control) | 5.0 | 63.6 | 1.0 |
| F | 5.0 | 67.1 | 1.0 |

TABLE 3-continued
COLOR EFFECTS DUE TO GAMMA IRRADIATION AFTER SHORT TERM DARK AGING

| SAMPLE (CONTROLS) | GAMMA IRRADIATION EXPOSURE (MRAD) | COLOR CHANGE DUE TO GAMMA IRRADIATION (DELTA YI) | ELAPSED TIME AFTER GAMMA IRRADIATION IS COMPLETED UNTIL COLOR IS MEASURED (DAYS) |
| --- | --- | --- | --- |
| F | 5.0 | 63.4 | 1.0 |
| E (control) | 7.5 | 79.1 | 4.0 |
| F | 7.5 | 78.1 | 4.0 |
| F | 7.5 | 78.2 | 4.0 |

Note:
These samples were all stored in the dark until YI measurements were made.

TABLE 4
COLOR EFFECTS DUE TO GAMMA IRRADIATION AFTER LIGHT AGING

| SAMPLE (CONTROLS) | GAMMA IRRADIATION EXPOSURE (MRAD) | COLOR CHANGE DUE TO GAMMA IRRADIATION (DELTA YI) | ELAPSED TIME AFTER GAMMA IRRADIATION IS COMPLETED UNTIL COLOR IS MEASURED (DAYS) |
| --- | --- | --- | --- |
| E (control) | 2.5 | 10.7 | 8.8 |
| E (control) | 2.5 | 11.4 | 8.8 |
| F | 2.5 | 10.3 | 8.8 |
| F | 2.5 | 10.6 | 8.8 |
| E (control) | 5.0 | 49.9 | 7.9 |
| E (control) | 5.0 | 45.4 | 7.9 |
| F | 5.0 | 34.8 | 7.9 |
| F | 5.0 | 31.5 | 7.9 |
| E (control) | 7.5 | 71.9 | 8.1 |
| F | 7.5 | 64.3 | 8.1 |
| F | 7.5 | 64.3 | 8.1 |

Note:
These samples are shown after lab aging under fluorescent lights after YI measurements reported in Table 3, supra.

TABLE 5
COLOR EFFECTS DUE TO GAMMA IRRADIATION AFTER LIGHT AGING

| SAMPLE (CONTROLS) | GAMMA IRRADIATION EXPOSURE (MRAD) | COLOR CHANGE DUE TO GAMMA IRRADIATION (DELTA YI) | ELAPSED TIME AFTER GAMMA IRRADIATION IS COMPLETED UNTIL COLOR IS MEASURED (DAYS) |
| --- | --- | --- | --- |
| C | 2.5 | 3.7 | 8.9 |
| C | 2.5 | 3.3 | 8.9 |
| D (control) | 2.5 | −10.8 | 8.9 |
| D (control) | 2.5 | −11.8 | 8.9 |
| C | 5.0 | 6.2 | 7.9 |
| C | 5.0 | 6.2 | 7.9 |
| D (control) | 5.0 | −22.2 | 7.9 |
| D (control) | 5.0 | −23.8 | 7.9 |
| C | 7.5 | 9.2 | 8.1 |
| C | 7.5 | 10.9 | 8.1 |
| D (control) | 7.5 | −29.2 | 8.1 |
| D (control) | 7.5 | −30.6 | 8.1 |

Note:
These samples are reported after lab aging under fluorescent lights following YI measurements reported in Table 2, supra.

TABLE 6
COLOR EFFECTS DUE TO GAMMA IRRADIATION AFTER LIGHT AGING

| SAMPLE (CONTROLS) | GAMMA IRRADIATION EXPOSURE (MRAD) | COLOR CHANGE DUE TO GAMMA IRRADIATION (DELTA YI) | ELAPSED TIME AFTER GAMMA IRRADIATION IS COMPLETED UNTIL COLOR IS MEASURED (DAYS) |
| --- | --- | --- | --- |
| A | 2.5 | 5.6 | 8.9 |
| A | 2.5 | 5.5 | 8.9 |
| B | 2.5 | −21.1 | 8.9 |
| B | 2.5 | −20.5 | 8.9 |
| A | 5.0 | 17.2 | 7.9 |
| B | 5.0 | −38.4 | 7.9 |
| A | 7.5 | 32.8 | 8.1 |
| B | 7.5 | −53.2 | 8.1 |

Note:
These samples reported after lab aging under florescent lights following YI measurements reported in Table 1, supra.

As can be seen from the data, polycarbonate resin turns yellow (increasing YI) with gamma ray irradiation and amorphous nylon turns a blue-purple (decreasing YI) with gamma ray irradiation. Neither the polycarbonate nor amorphous nylon samples maintain this color. The color immediately begins decaying back to the sample's original color with increasing time. As shown by the two blend samples (C and F), the color generated by irradiation of blends of polycarbonate and amorphous nylon are less than the colors generated by irradiation of either pure material. Thus, the blends will show improved color.

What is claimed is:

1. An article of improved color, molded from a thermoplastic molding composition, which comprises;
   from about 10–90 percent by weight of an aromatic polycarbonate resin; and
   from about 10–90 percent by weight of an amorphous polyamide resin;
   said article having been subjected to sterilization by ionizing radiation.

2. An article of claim 1 wherein the polycarbonate resin contains structural units of the formula:

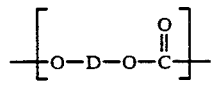

wherein D is divalent aromatic radical.

3. An article of claim 2 wherein aromatic polycarbonate resin comprises polymers selected from the group consisting of poly(ester-carbonate) polymers.

4. An article of claim 2 wherein the aromatic polycarbonate is obtained by polymerizing phosgene with 2,2-bis(4-hydroxyphenyl) propane.

5. An article of claim 4 wherein the aromatic polycarbonate is obtained by polymerizing phosgene with 2,2-bis(4-hydroxyphenol) propane and a mixture of isophthalic and terephthalic acids.

6. An article of claim 1 wherein the weight ratio of amorphous polyamide to polycarbonate is about 1:1.

7. An article of claim 1 wherein the amorphous polyamide contains structural units selected from those of the formula:

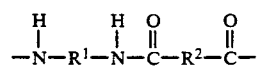

-continued or

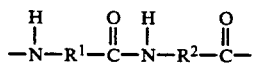

wherein in $R^1$ and $R^2$ are different divalent organic radicals selected from the group consisting of $C_2$–$C_{15}$ alkylene radicals $C_3$–$C_{18}$ cycloalkylene radicals and $C_6$ to $C_{20}$ arylene radicals.

8. An article of claim 7 wherein the amorphous polyamide is obtained by polymerization of members selected from the group consisting of
   (a) terephthalic acid with, trimethylhexamethylene diamine;
   (b) isophthalic acid with trimethylhexamethylene diamine;
   (c) adipic acid, azelaic acid and 2,2-bis-(p-aminocyclohexyl) propane;
   (d) terephthalic acid with bis (4-amino cyclohexyl) methane;
   (e) isophthalic acid with hexamethylenediamine;
   (f) terephthalic acid/isophthalic acid with hexamethylene diamine, and
   (g) adipic acid/azelaic acid with diphenyl methane diisocyanate.

9. An article of claim 1 which further comprises an impact-modifying proportion of a polyamide-polyether block copolymer having recurring chain units of the formula:

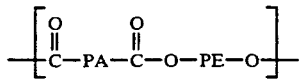

wherein PA represents a saturated amide sequence formed from a lactam or an amino acid having a hydrocarbon chain containing from 4 to 14 carbon atoms, inclusive, or from a dicarboxylic acid and a diamine wherein both can have from 4 to 40 carbon atoms, inclusive; and PE represents a polyether sequence formed from a polyoxyalkylene glycol.

10. An article of claim 9 wherein the proportion by weight of the polyoxyalkylene glycol sequence to the total weight of the block copolymer is from 5 to 85 percent.

11. An article of claim 9 wherein the impact-modifying proportion is from 5 to 30 weight percent of the blend.

12. A method of preparing a thermally molded, sterile, article of improved color which comprises;
   providing the article molded in a solid form from a blend which comprises;
   from about 40–60 percent by weight of an aromatic polycarbonate resin; and
   from about 40–60 percent by weight of an amorphous polyamide resin;
   sealing the article in a moisture-proof, microorganism-impermeable, ionizing ray-permeable container; and
   subjecting the sealed-in article to a non-destructive, sterilizing dose of an ionizing ray.

* * * * *